United States Patent [19]

Mayer et al.

[11] Patent Number: 5,090,387
[45] Date of Patent: Feb. 25, 1992

[54] METHOD AND ARRANGEMENT FOR CHECKING THE OPERATIONAL CAPABILITY OF AN EXHAUST-GAS PROBE HEATER AND THE SUPPLY SYSTEM THEREOF

[75] Inventors: Rudi Mayer, Vaihingen/Enz; Helmut Denz, Stuttgart; Ernst Wild, Oberriexingen; Rainer Frank, Sachsenheim, all of Fed. Rep. of Germany

[73] Assignee: Robert Bosch GmbH, Stuttgart, Fed. Rep. of Germany

[21] Appl. No.: 684,908

[22] PCT Filed: Jul. 26, 1990

[86] PCT No.: PCT/DE90/00569

§ 371 Date: Apr. 30, 1991

§ 102(e) Date: Apr. 30, 1991

[87] PCT Pub. No.: WO91/03636

PCT Pub. Date: Mar. 21, 1991

[30] Foreign Application Priority Data

Aug. 30, 1989 [DE] Fed. Rep. of Germany ....... 3928709

[51] Int. Cl.⁵ .................................. F02M 51/00
[52] U.S. Cl. ..................... 123/479; 123/489; 123/440
[58] Field of Search ............. 123/479, 440, 489, 480, 123/434; 204/401, 406, 425; 364/431.03, 431.04, 431.11

[56] References Cited

U.S. PATENT DOCUMENTS

| | | | |
|---|---|---|---|
| 3,916,848 | 11/1975 | Schmidt | 123/479 |
| 4,094,186 | 6/1978 | Wessel | 123/479 |
| 4,419,190 | 12/1983 | Dietz et al. | 204/1 T |
| 4,721,088 | 1/1988 | Mieno et al. | 123/489 |
| 4,742,808 | 5/1988 | Blümel et al. | 123/479 |
| 4,777,922 | 10/1988 | Mieno et al. | 123/489 |
| 4,844,038 | 7/1989 | Yamato et al. | 123/489 |
| 4,938,194 | 7/1990 | Kato et al. | 204/406 |
| 4,951,632 | 8/1990 | Yakuwa et al. | 123/440 |
| 4,958,611 | 9/1990 | Uchimami et al. | 204/401 |
| 4,980,834 | 12/1990 | Ikada et al. | 364/431.11 |
| 4,986,242 | 1/1991 | Bonfiglioli et al. | 123/479 |
| 5,003,954 | 4/1991 | Yakuwa et al. | 123/479 |
| 5,054,452 | 10/1991 | Denz | 123/479 |

FOREIGN PATENT DOCUMENTS

| | | | |
|---|---|---|---|
| 59-028046 | 6/1984 | Japan | 123/479 |
| 61-116043 | 10/1986 | Japan | 123/479 |
| 62-157255 | 12/1987 | Japan | 123/479 |

*Primary Examiner*—Raymond A. Nelli
*Attorney, Agent, or Firm*—Walter Ottesen

[57] ABSTRACT

A method and an arrangement for carrying out the method are proposed whose fundamental concept is to perform a diagnosis of the heating device of an exhaust-gas probe, which emits a control signal for closed-loop controlling the air/fuel mixture of an internal combustion engine. The diagnosis is based on that the exhaust-gas probe is heated more rapidly because of the switching-in of the heating device than by mere heating by the exhaust gases which flow past the exhaust-gas probe. The heating device includes at least the probe heater, devices which supply the probe heater with the necessary heating power, and the supply leads therefor.

8 Claims, 2 Drawing Sheets

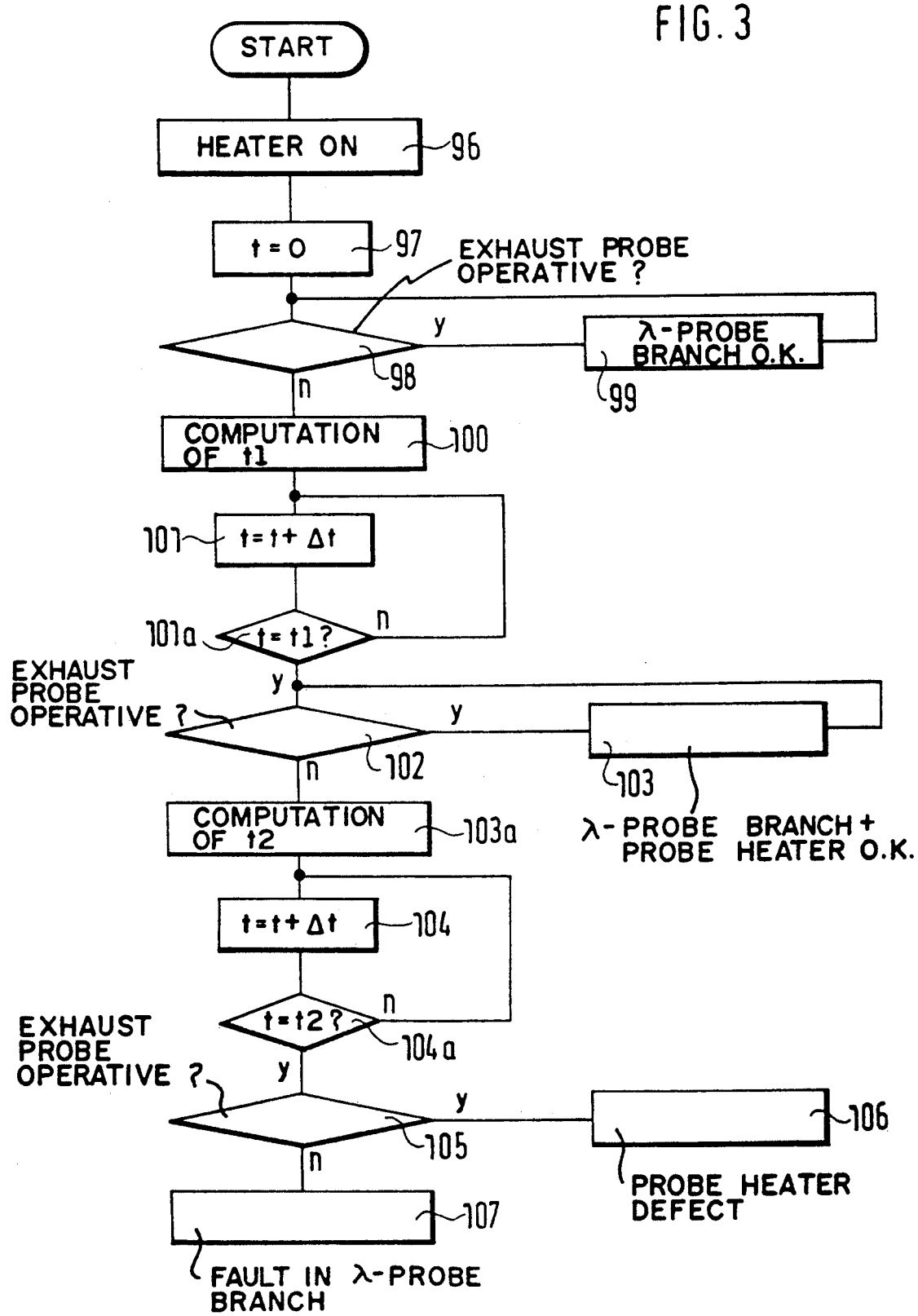

METHOD AND ARRANGEMENT FOR CHECKING THE OPERATIONAL CAPABILITY OF AN EXHAUST-GAS PROBE HEATER AND THE SUPPLY SYSTEM THEREOF

FIELD OF THE INVENTION

The method according to the invention and the arrangement specified for the performance of the method relate to the checking of the operational capability of a heater for an exhaust-gas probe and the supply system thereof.

BACKGROUND OF THE INVENTION

It is known to provide control arrangements in order to maintain a specific air/fuel ratio of the air/fuel mixture supplied to an internal combustion engine which obtain their control variable from an oxygen measuring probe mounted in the exhaust-gas system of the internal combustion engine. This control is generally superposed on a known mixture control arrangement by which the air/fuel mixture is roughly controlled in a preliminary manner. It is a condition for the smooth functioning of such control arrangement that the oxygen measuring probe works smoothly. In the case of the known oxygen measuring probes, operational readiness is only ensured after a certain operating temperature has been reached. For this reason, a mixture open-loop control must be provided for the cold start and the running up of the internal combustion engine in the case of probes which are heated up by the exhaust gases of the internal combustion engine. This mixture open-loop control is only replaced by the mixture closed-loop control when the probe temperature rising with the operating temperature of the internal combustion engine is reached.

The operational readiness of an oxygen probe with an ion-conducting solid-state device can be monitored in various ways. Thus, a monitoring arrangement is known from German Patent 2,301,354 in which voltage signals having variable potential and emitted by the oxygen measuring probe at short intervals determined by operating conditions are transmitted via a threshold switch to a timing element. As a consequence of these signals, the timing element holds a switch in a first switch position as long as the time interval of the voltage signals is shorter than the switching time of the timing element. In the other case, the switch is brought into a second switch position after this switching time has elapsed. By means of this switch, the operating mixture can then be influenced or a warning device can be switched on.

This arrangement has the disadvantage that it merely detects the total failure of the oxygen measuring probe when this probe no longer emits a signal with variable voltage because of a fault or at too low a temperature.

A method and an arrangement for monitoring the operational readiness of an oxygen measuring probe are presented in German Patent 2,608,245 which are already able to detect with certainty the operating conditions having reduced operational readiness of the oxygen measuring probe. In these cases, the mixture closed-loop control arrangement otherwise operated by means of the probe can be converted to a mixture open-loop control arrangement as early as possible. That is, as soon as the oxygen measuring probe emits a sufficiently high voltage signal for reliable operation of the closed-loop control arrangement.

This is effected by determining two voltage threshold values corresponding to the minimum and maximum voltage emitted by the probe when it is operationally ready. As soon as the increasing output voltage of the oxygen measuring probe resulting from the rising temperature exceeds these determined threshold values, this is detected by the comparator devices. The mixture open-loop control arrangement is switched off with insertion of a timing element and, when the signal change per time unit is less frequent, the mixture open-loop control arrangement is switched on again.

A method for recognizing the operational readiness of an oxygen measuring probe is known form the European patent application U.S. Pat. No. 4,742,808 wherein an exact measurement of the internal resistance of the oxygen measuring probe is made. A criterion for the operational readiness is given by the subsequent comparison with a predetermined value.

A method and an arrangement for controlling the temperature of an exhaust-gas probe are known from U.S. Pat. No. 4,419,190 which convert the temperature-dependent electrical resistance of the oxygen measuring probe into a temperature signal and then activate a heater device for heating the exhaust-gas probe. The operating temperature of the exhaust-gas probe can thereby be kept constant in a simple manner and without additional sensors and measurement leads.

In order that the exhaust-gas sensor may reach its operating temperature as quickly as possible and can subsequently also be kept at a predetermined temperature, it is prerequisite that the heater for the exhaust-gas probe, in the following called probe heater, be operationally ready.

SUMMARY OF THE INVENTION

The method and arrangement of the invention afford the advantage that they monitor the operational readiness of the probe heater without additional sensors or leads. Advantageous further developments and embodiments are the subject matter of the dependent claims.

Only when the probe heater is functioning properly can it be ensured that the exhaust-gas probe reaches its operating temperature quickly and also retains this temperature during operation. Otherwise the probe heats up substantially slower in dependence upon the exhaust-gas temperature and composition and can, for instance in overrun operation, cool down again. This has the consequence that the ratio of the air/fuel mixture supplied to the internal combustion engine is determined more frequently by the open-loop control which is not able to maintain the desired air/fuel ratio as accurately as the closed-loop control. This results in exhaust-gas emissions with a higher proportion of noxious constituents.

If it is however determined by the method of the invention that the probe heater is not operationally ready, this can be made known to the driver for example by an indicator light. The driver can then take appropriate measures to restore the operational readiness of the probe heater.

The method of the invention further checks the operational readiness of the exhaust-gas probe. When this operational readiness is not present, this can also be signalled to the driver.

With the foregoing, the requirements of the California Environmental Authority (CARB) are met which requires that the failure of parts affecting the exhaust gas (which includes the probe heater) is detected and indicated.

BRIEF DESCRIPTION OF THE DRAWINGS

The invention will now be described with reference to the drawings wherein.

DESCRIPTION OF THE PREFERRED EMBODIMENTS OF THE INVENTION

The basic concept of the invention comprises performing a diagnosis of the heating device of an exhaust-gas probe which heating device emits a measuring signal, preferably for controlling the air/fuel mixture for an internal combustion engine. The diagnosis is based on the exhaust-gas probe being heated more rapidly than it would be heated merely by the exhaust gases flowing past the exhaust-gas probe by switching on a heating device which comprises at least the probe heater, devices which supply the necessary electrical power to the probe heater and the supply lines corresponding thereto.

Before discussing the invention in the following, it is expressly pointed out that the block diagram, illustrated in FIG. 1 and showing the invention by means of discrete switching stages, does not limit the invention, but serves particularly to illustrate the basic functions of the invention and to show the specific functional sequences in one possible form of realizing the invention. It is understood that the individual modules and blocks can be constructed according to analog, digital or even hybrid technology. It is further also possible that they can comprise, wholly or partially condensed, appropriate areas of program-controlled digital systems, for example microcomputers, microprocessors, digital or analog logic elements and the like. The descriptions given subsequently are therefore merely to be regarded as a preferred embodiment of the overall function and time sequence, the function accomplished at the particular blocks being discussed, and of the particular coordination of the subfunctions represented by the individual components, whereby the references to the particular circuit blocks are made for better understanding.

Figure 1:
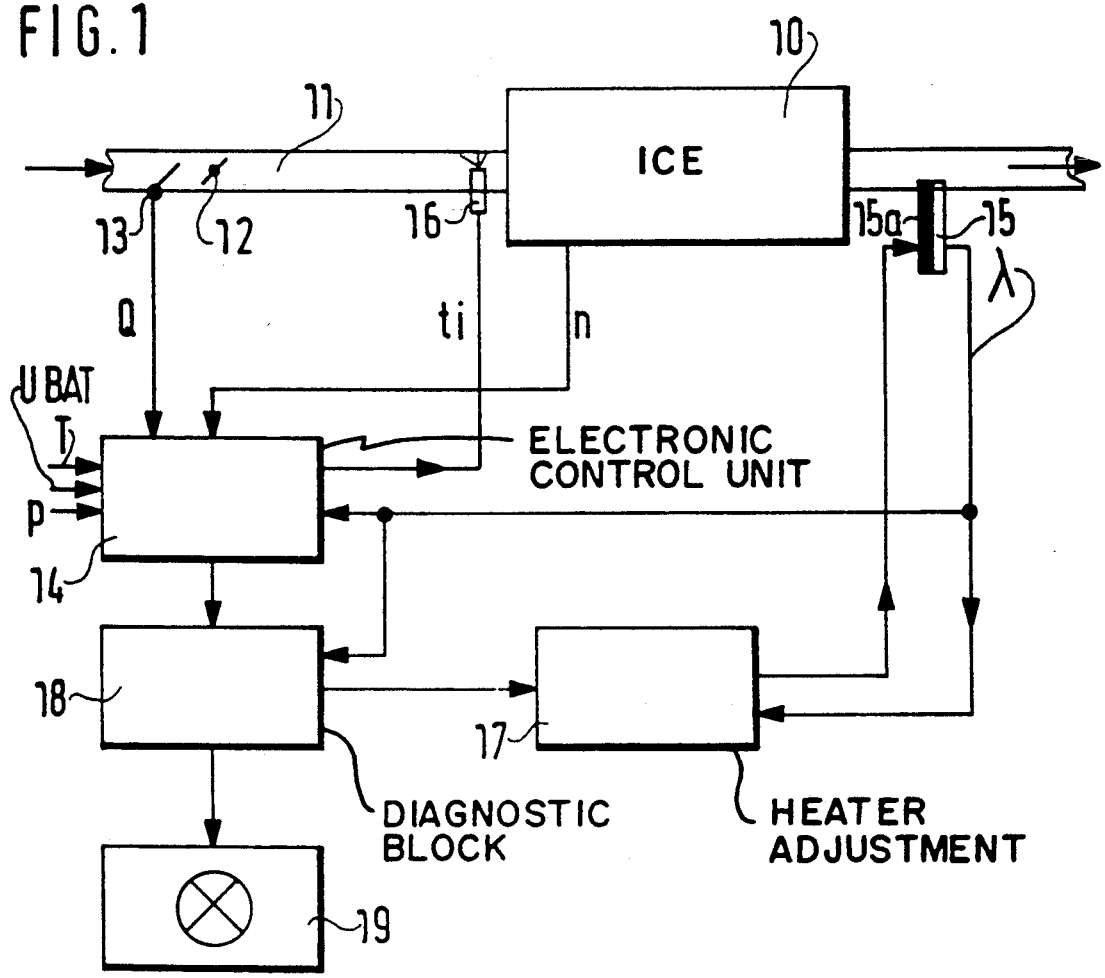
FIG. 1 is a simplified schematic block diagram of one possible embodiment including electronic and electrical closed-loop and open-loop control elements and actuators for the operation of an internal combustion engine.

FIG. 1 shows an internal combustion engine 10 with its intake region 11 wherein, inter alia, a throttle flap 12 is mounted and the displacement of which from the rest position determines the volume of air which is supplied to the internal combustion engine 10. An air volume measuring device 13 which measures this volume of air, gives an output signal Q to an electronic control unit 14 which is usually a microcomputer with microprocessor, corresponding memory and power supply and which receives further data of operating conditions such as: speed n of the internal combustion engine; the air/fuel ratio supplied to the internal combustion engine which is determined by the output signal of a lambda probe 15 provided in the exhaust-gas channel and an instantaneous value indication of the operating condition of the internal combustion engine at the time, obtained, more precisely, from the oxygen content of the exhaust gas.

From these data and a multiplicity of further information supplied such as temperature (T), air pressure (p) and the like ($U_{Bat}$,...), the electronic control unit 14 produces an output signal computed with great precision, in the case of a fuel-injection system, for example, an injection control command ti for controlling the injection valves, symbolically represented by 16 in the intake region.

The exhaust-gas probe is provided with a probe heater 15a which is supplied with electric power by a heater controller 17 in such a manner that the exhaust-gas probe 15 rapidly reaches its operating temperature and maintains it subsequently if required. The output signal or the internal resistance of the exhaust-gas probe 15 may for instance be used as signal for the temperature of the exhaust-gas probe 15.

In a simplified embodiment, a circuit element can be used instead of a heater controller which circuit element constantly switches in the probe heater during operation of the internal combustion engine.

A diagnostic block 18 is also provided for the performance of the diagnostic method which block is shown separately in FIG. 1 but can also be part of the central microcomputer. This diagnostic block receives signals of the electronic control unit 14 and the exhaust-gas probe 15 and emits control signals to the heater controller 17 and results of the diagnosis to an indicator device 19. The diagnostic block 18 further comprises memories in which the values of the signals received and the results determined therefrom can be stored; and, comparator means which can make the necessary comparisons of the values and results, also with regard to their variations in time.

The diagnostic block 18 can also drive an indicating device 19 which, depending on the result of the diagnosis, for example makes indicator lamps light up. It is understood that this indication can in principle be effected in any desired form, also as a letter display and can also indicate intermediate values of the diagnosis.

If the exhaust-gas probe is not operationally ready, the heater controller 17 receives a command via the electronic unit 14 and the diagnostic block 18 in order that the probe heater 15a is supplied with electric power.

The heating-up response of the exhaust-gas probe 15 depends on whether the probe heater is operable or not. It can be seen from FIG. 2 how the probe temperature determined from temperature dependent values changes when the exhaust-gas probe is heated only by the exhaust gases flowing past it (a) or if it is heated additionally by the probe heater 15a (b).

Figure 2:
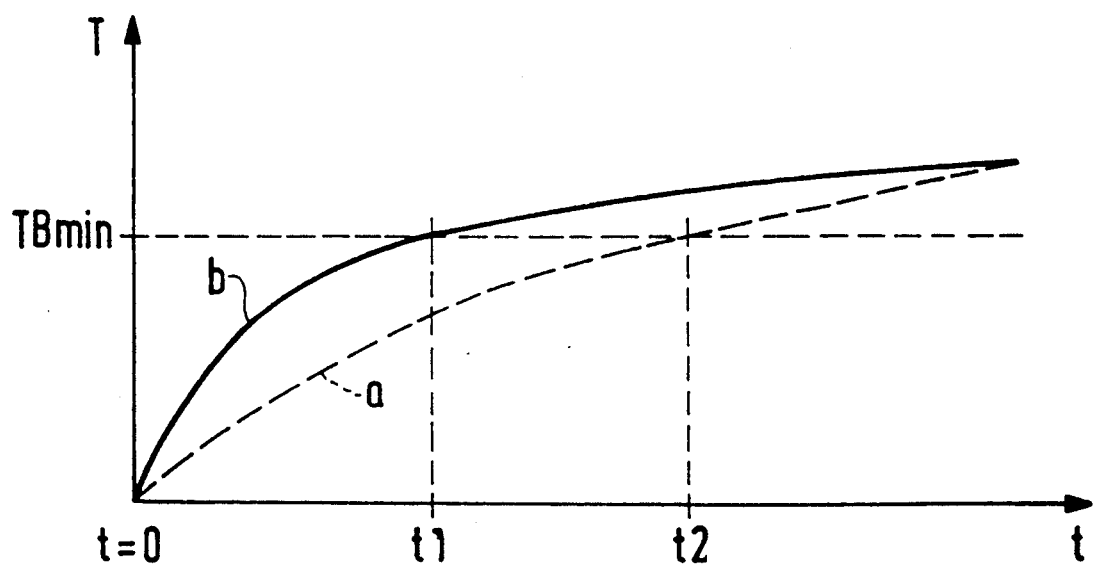
FIG. 2 is the heat-up response of an exhaust-gas probe as a function of time with and without the probe heater; and, FIG. 3 is a flowchart of a first embodiment of the diagnostic method.

The temperature variations shown in FIG. 2 are only schematic and merely facilitate better understanding of the invention. It can be seen that, with the exhaust-gas probe being merely heated by the exhaust gases flowing past the probe (a), the minimum operating temperature TBmin is reached later (t2) than if in addition the probe heater is in operation (t1).

It is specifically pointed out that the times t1 and t1 depend on operating values of the internal combustion engine, for example: the temperature of the internal combustion engine 10 at its start (t=0); the temperature of the exhaust-gas probe 15 at t=0; the load and the rotational speed of the internal combustion engine; the air/fuel ratio of the mixture supplied to the internal combustion engine; and, the sum of the injection times emitted which represents a measure of the exhaust-gas heat quantity supplied by the engine.

The sequence of the diagnostic method is explained with the aid of FIG. 3.

The method of the invention is always started when the internal combustion engine is put into operation. After the heater is switched on (step 96), the time counter is started (step 97) and it is subsequently checked in step 98 whether the exhaust-gas probe is operationally ready. This can for instance be done by evaluating the internal resistance of the exhaust-gas probe as a measure of the temperature, or, it is checked whether the signal emitted by the exhaust-gas probe has already amplitudes from which operational readiness can be concluded. If this is the case, for example during restarting the internal combustion engine after a brief standstill, it is concluded in step 99 that the supply system of the exhaust-gas probe is operational. The result can be indicated by the indicator device 19 and/or stored in memories contained in the diagnostic block 20 which are provided for this purpose.

After performing step 99, the method again performs step 98. The loop consisting of steps 98 and 99 is run through as long as the exhaust-gas probe is operational.

If the exhaust-gas probe is not operationally ready, from the start of the method of the invention or only after some time, then the result of the inquiry in step 98 is "no" and the method is continued with step 100 in which the first predetermined time t1 (see also FIG. 2) can be computed, for example on the basis of the operating values of the internal combustion engine.

In steps 101 and 101a, there is a wait controlled by a timing element until the first pregiven time t1, starting from step 97 (t=0), has elapsed and then, in step 102, in a similar manner to that in step 98, an inquiry follows whether the exhaust-gas probe is operationally ready.

If operational readiness is determined in step 102 (yes), then it is concluded in step 103 that the probe heating system, the probe and also its supply system are operable. The result from step 103 can be indicated by the indicator device 19 and/or can be stored in memories provided for this purpose.

After step 103 has been performed, the method again performs step 102. The loop consisting of steps 102 and 103 will be run through as long as the exhaust-gas probe remains operationally ready.

If the inquiry in step 102 reveals that the exhaust-gas probe suddenly is no longer operationally ready, which can for instance be caused by a fault in the probe supply system, then the method continues with step 103a.

If the result of the inquiry in step 102 is "no", the second predetermined time t2 can be computed in step 103a in a manner similar to that in step 100.

In steps 104 and 104a there is a wait controlled by a timing element until the predetermined time t2, starting from step 97 (t=0), has elapsed. And it is checked in step 105, in a similar manner to that in step 98, whether the exhaust-gas probe is operationally ready or not. If "yes", it is concluded in step 106 that there is a fault in the probe heater system. This result can be indicated and/or stored.

The conclusion from step 106 is justified because the exhaust-gas probe, which is only operationally ready if the minimum operating temperature has been attained, has become operationally ready after a time t2 which is sufficient to heat up the exhaust-gas probe by the surrounding exhaust gases alone. It must be ensured that the pregiven times t1 and t2 have been so determined that the minimum operating temperature could be reliably reached.

If the exhaust-gas probe is not yet operationally ready after the pregiven time, it is concluded in step 107 that there is a fault in the λ-probe branch.

It should be additionally mentioned that the results of the diagnosis from steps 99, 103, 106 and 107 can be indicated to the driver by the indicator device 19 and/or can be stored in the memories provided for this purpose and forming part of the diagnostic block 18.

It is further self-evident that the pregiven times t1 and t2 do not have to be computed and measured from a common point of time t=0 (step 97). Since, to be more precise, it is a matter of time intervals t1 and t2, each of these time intervals can have a different reference point, for example the start of the computation concerned.

If is is determined that the exhaust-gas probe is not operationally ready, it is also possible for a signal to be emitted by means of which the electronic control unit switches from closed-loop control to open-loop control.

The essential point of the diagnostic method of the invention is that the operational capability of the probe heater system is checked with the heating system comprising the probe heater 15a, the heater controller 17 and the connecting leads corresponding thereto. This is done by evaluating the variations in time of electrical, temperature-dependent values which can be obtained from the signal of the exhaust-gas probe 15. For this purpose, it is necessary that the exhaust-gas probe can be heated to its operating temperature by the probe heater system and, though more slowly, by the exhaust gases surrounding it.

These exhaust gases can stem from various combustion processes, as are for example found in internal combustion engines and heating installations.

From this it becomes clear that the method of the invention is not limited to the checking of heating devices for exhaust-gas probes used to control an internal combustion engine. It is instead also possible to monitor heating devices of probes which measure the exhaust-gas composition of heating installations or other chemical or combustion processes.

The method of the invention has the particular advantage that it works independently of additional sensors and can therefore be cost-effectively realized.

We claim:

1. A method for monitoring the operational readiness of an exhaust-gas probe, which is only operationally ready above a given temperature and is provided with a probe heater for more rapid heating and for maintaining an operating temperature range, the method comprising the steps of:
   switching the probe heater on;
   then detecting the operational readiness of the probe at two predetermined times t1 and t2 following one upon the other, the predetermined times t1 and t2 being matched to the heat-up response of the probe; and,
   if the lack of operational readiness is determined after the elapse of the predetermined time t1 and if the operational readiness is determined after the elapse of the pregiven time t2, concluding failure of the probe heater; and, activating a diagnosis or warning device.

2. The method for monitoring the operational readiness of an exhaust-gas probe of claim 1, the method comprising determining the functional capability of the probe heater and/or the supply system of the exhaust-gas probe with the following additional steps:

(a) switching in the probe heater system;

(b) inquiring whether the exhaust-gas probe is operationally ready;

(c) if the exhaust-gas probe is operationally ready, it follows as the first possible diagnostic result that the exhaust-gas probe and its supply system are capable of functioning and the steps (b) and (c) are continuously repeated;

(d) if it has been determined in step (b) that the exhaust-gas probe is not operationally ready, but it is determined after a first predetermined time t1 that the exhaust-gas probe is operationally ready, it follows as second possible diagnostic result: that the exhaust-gas probe, the λ-probe branch and the probe heater are operable and step (d) is continuously repeated;

(e) if it was determined in step (d) that the exhaust-gas probe is not operationally ready, it is checked again after a second predetermined time t2 whether the exhaust-gas probe is operationally ready;

(f) if it is, it follows as a third possible diagnostic result that the exhaust-gas probe and the λ-probe branch are operable but the probe heater system is not operable;

(g) otherwise it follows as a fourth possible diagnostic result that there is a fault in the λ-probe branch; and, (h) indicating and/or storing of at least one of the above possible diagnostic results.

3. The method of claim 1, wherein the first predetermined time t1 and/or the second predetermined time t2 are computed in dependence on the operating characteristic variables of a device for which the composition of the exhaust gas is to be determined.

4. The method of claim 1, wherein the exhaust-gas probe is used to closed-loop control the air/fuel ratio of an air/fuel mixture supplied to an internal combustion engine.

5. The method of claim 1, wherein the operational readiness of the exhaust-gas probe is concluded from the following: an evaluation of electrical values of the exhaust-gas probe such as the internal resistance; the emitted voltage; and/or, the current flowing through the exhaust-gas probe.

6. An arrangement for monitoring the operational readiness of an exhaust-gas probe, which is only operationally ready above a given temperature and is provided with a probe heater for more rapid heating and for maintaining an operating temperature range, the arrangement comprising:

means for detecting the operational readiness of the probe after the probe heater is switched in at two consecutive pregiven times t1 and t2 and for matching the pregiven times t1 and t2 to the heat-up response of the probe;

means for concluding a failure of the probe heater after determining a lack of operational readiness after the pregiven time t1 has elapsed and, after determining operational readiness after the pregiven time t2 has elapsed; and, means for performing a diagnosis or activating a warning.

7. The arrangement of claim 6 further comprising:

means for switching on a probe heater current;

means for determining whether the exhaust-gas probe is operationally ready;

means for comparing the pregiven times t1 and t2 to the actual elapsed times;

means for concluding whether the probe heater and/or the supply system connected to the exhaust-gas probe is operable in dependence upon whether the exhaust-gas probe is operationally ready at the start or after the elapse of the time t1 or t2; and, means for indicating and/or storing the results of the diagnosis.

8. The arrangement of claim 7, further comprising means for determining the pregiven times t1 and/or t2 on the basis of the characteristic operating values of a device for which the composition of the exhaust gas is to be determined.

* * * * *

UNITED STATES PATENT AND TRADEMARK OFFICE
CERTIFICATE OF CORRECTION

PATENT NO. : 5,090,387
DATED : February 25, 1992
INVENTOR(S) : Rudi Mayer, Helmut Denz, Ernst Wild and Rainer Frank It is certified that error appears in the above-identified patent and that said Letters Patent is hereby corrected as shown below:

In column 1, line 42: delete "German Patent 2,301,354" and substitute -- United States Patent 3,916,848 -- therefor.

In column 1, line 61: delete "German Patent 2,608,245" and substitute -- United States Patent 4,094,186 -- therefor.

In column 2, lines 15 and 16: delete "form the European patent application" and substitute -- from -- therefor.

In column 4, line 61: delete "t1" (second occurrence) and substitute -- t2 -- therefor.

In column 6, line 17: delete "is" (first occurrence) and substitute -- it -- therefor.

In column 6, line 60: delete "the" and substitute -- a -- therefor.

In column 6, line 63: between "concluding" and "failure", insert -- a --.

Signed and Sealed this

Fifteenth Day of June, 1993

Attest:

MICHAEL K. KIRK

Attesting Officer

Acting Commissioner of Patents and Trademarks